US00PP20298P2

(12) United States Plant Patent
Mooney

(10) Patent No.: US PP20,298 P2
(45) Date of Patent: Sep. 15, 2009

(54) SIBERIAN CYPRESS PLANT NAMED 'CONDREW'

(50) Latin Name: *Microbiota decussata*
Varietal Denomination: Condrew

(75) Inventor: Andrew R. Mooney, Lancaster, PA (US)

(73) Assignee: CP Delaware, Inc., Wilmington, DE (US)

( * ) Notice: Subject to any disclaimer, the term of this patent is extended or adjusted under 35 U.S.C. 154(b) by 8 days.

(21) Appl. No.: 12/213,770

(22) Filed: Jun. 24, 2008

(51) Int. Cl.
*A01H 5/00* (2006.01)

(52) U.S. Cl. ..... Plt./213

(58) Field of Classification Search ..... Plt./213
See application file for complete search history.

*Primary Examiner*—Annette H Para
(74) *Attorney, Agent, or Firm*—Buchanan, Ingersoll & Rooney PC

(57) ABSTRACT

A new and distinctive *Microbiota decussata* plant is provided. Unlike common plants of the species, the new plant displays attractive foliage that is bluer in coloration particularly at the juvenile stage and during the winter months. The growth habit is prostrate, and more creeping than that of the 'Condavis' cultivar (U.S. Plant patent application Ser. No. 12/071,395, filed Feb. 20, 2008). The new plant is well suited for growing as a specimen plant or in a group as a ground cover.

2 Drawing Sheets

Botanical/commercial classification: *Microbiota decussata*/Siberian Cypress.
Varietal denomination: cv. Condrew.

SUMMARY OF THE INVENTION

The present invention is a new and distinct Siberian Cypress cultivar, botanically known as *Microbiota decussata. Microbiota* is recognized to be a genus of evergreen coniferous shrub in the cypress family Cupressaceae, containing only one species of *Microbiota decussata.* Such species is believed to have originated in the Russian Far East, and sometimes is identified by the common names of Siberian Cypress, Cypress, and Russian arborvitae.

The new plant of the present invention was discovered as a naturally-occurring branch sport of unknown causation which appeared in a nursery setting on a common *Microbiota decussata* plant. The discovery was made during September, 1996 at West Grove, Pa., U.S.A. I was attracted to a single branch of a single plant of the species primarily in view of the distinctive appearance of the foliage which was unlike that of all other *Microbiota decussata* plants being grown in the nursery and otherwise known to me. The distinctive plant was carefully preserved and has thereafter undergone detailed observation and evaluation.

It was found that the new Siberian Cypress plant of the present invention displays the following combination of characteristics:

(a) displays a creeping prostrate growth habit, (b) forms attractive foliage that is bluer in coloration particularly at the juvenile stage and during the winter months, and (c) is well suited for growing as a specimen plant or in a group as a ground cover.

The plant grows well in U.S.D.A. Hardiness Zone Nos. 3 to 8.

The new cultivar can be readily distinguished from previously available *Microbiota decussata* plants upon an inspection of the growth habit in combination with the foliar coloration. A low-growing compact plant is provided which displays a distinctive foliar coloration. When compared to the 'Condavis' cultivar (U.S. Plant patent application Ser. No. 12/071,395, filed Feb. 20, 2008), the new cultivar of the present invention displays a more creeping growth habit and a bluer foliar coloration particularly during the winter months.

The new cultivar of the present invention can be grown to advantage to provide an attractive ornamental plant which can be grown as a specimen in the landscape or in groups to provide a continuous ground cover.

Asexual reproduction of the new cultivar by the use of cuttings has been carried out at West Grove, Pa., U.S.A. Commonly such asexual reproduction has been carried out in the winter while using semi-hardwood cuttings, Hormodin No. 3 rooting hormone and the use of bottom heating at approximately 70° F. to promote faster rooting. Such propagation has confirmed that the unique combination of characteristics of the new cultivar has been stably established and is well transmitted to successive generations. The new cultivar asexually reproduces in a true-to-type manner.

The new cultivar has been named 'Condrew' and will be marketed under the DREW'S BLUE trademark.

BRIEF DESCRIPTION OF THE PHOTOGRAPHS

The accompanying photographs show as nearly true as it is reasonably possible to make the same in color illustrations of this character, typical container-grown specimens of the new cultivar at an age of approximately five years while being grown at West Grove, Pa., U.S.A. For the first five to six months, the plants had been grown indoors during which time root development took place. The plants thereafter had been placed in larger containers and were grown outdoors with the protection of a sheet of plastic during the winter.

DETAILED DESCRIPTION

Figure 1:
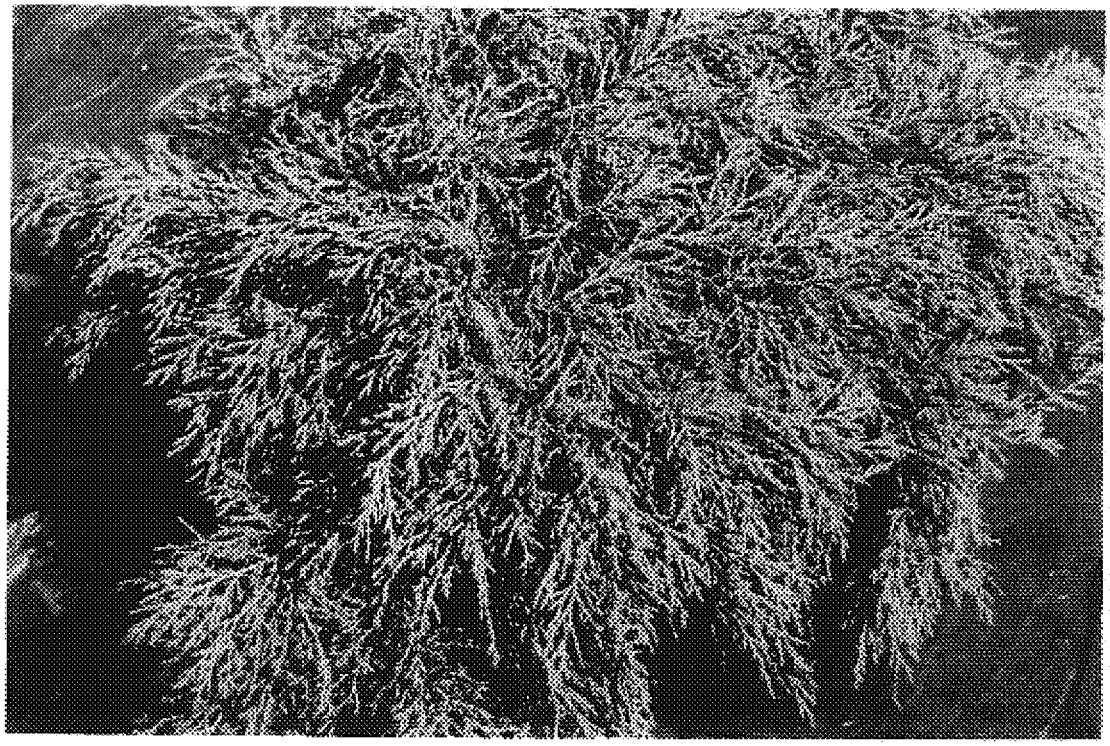
FIG. 1 shows from above a typical plant of the new cultivar during the Fall of 2007 wherein the attractive green foliage coloration with a hint of blue is shown.
Figure 2:
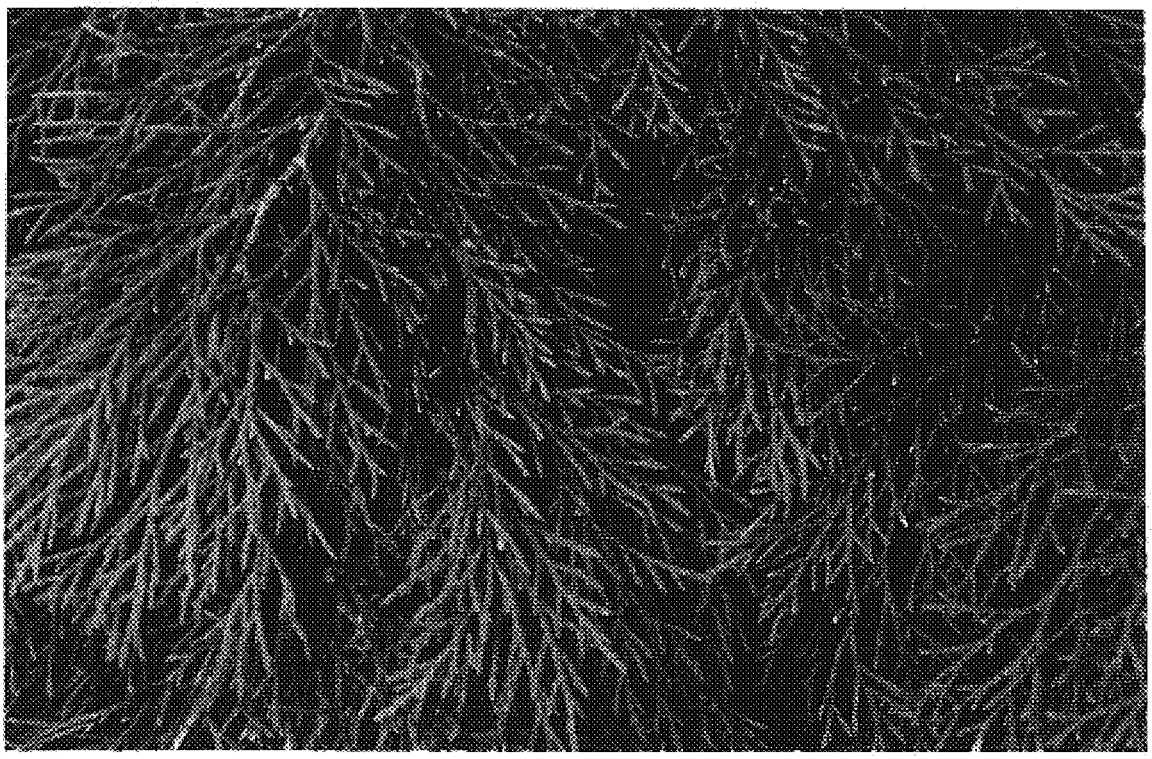
FIG. 2 shows for comparative purposes the summer coloration of a typical *Microbiota decussata* plant.
Figure 3:
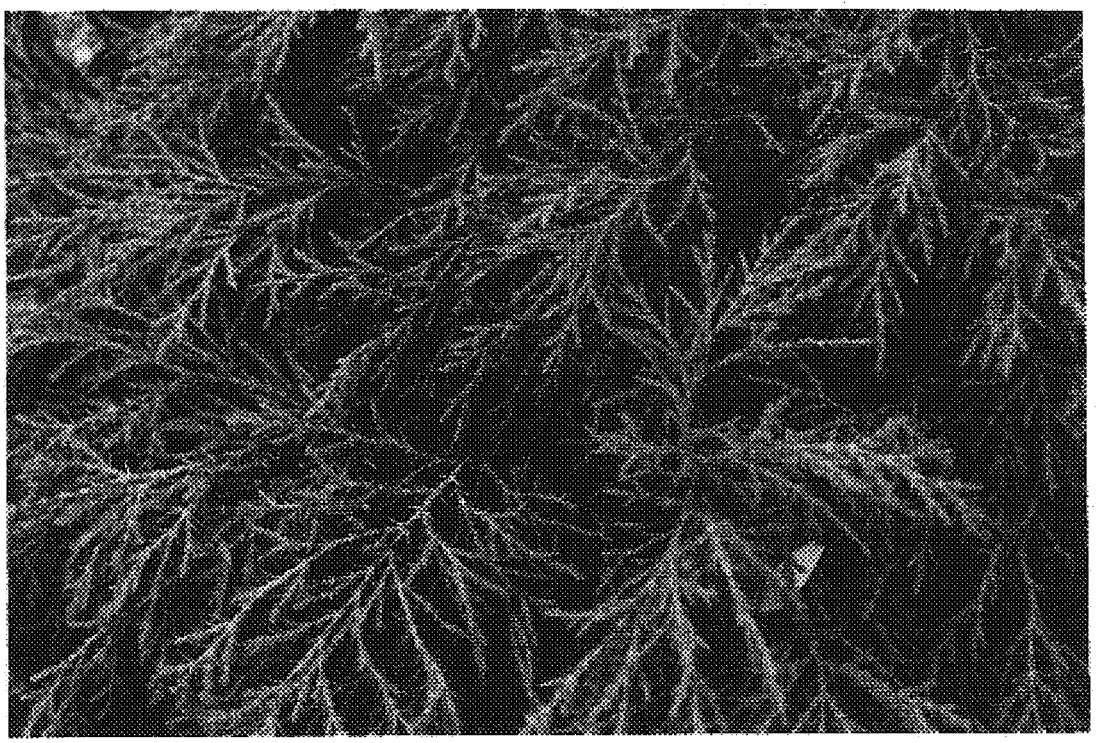
FIG. 3 shows the typical foliage of the new cultivar during the winter wherein a slightly blue coloration is visible.
Figure 4:
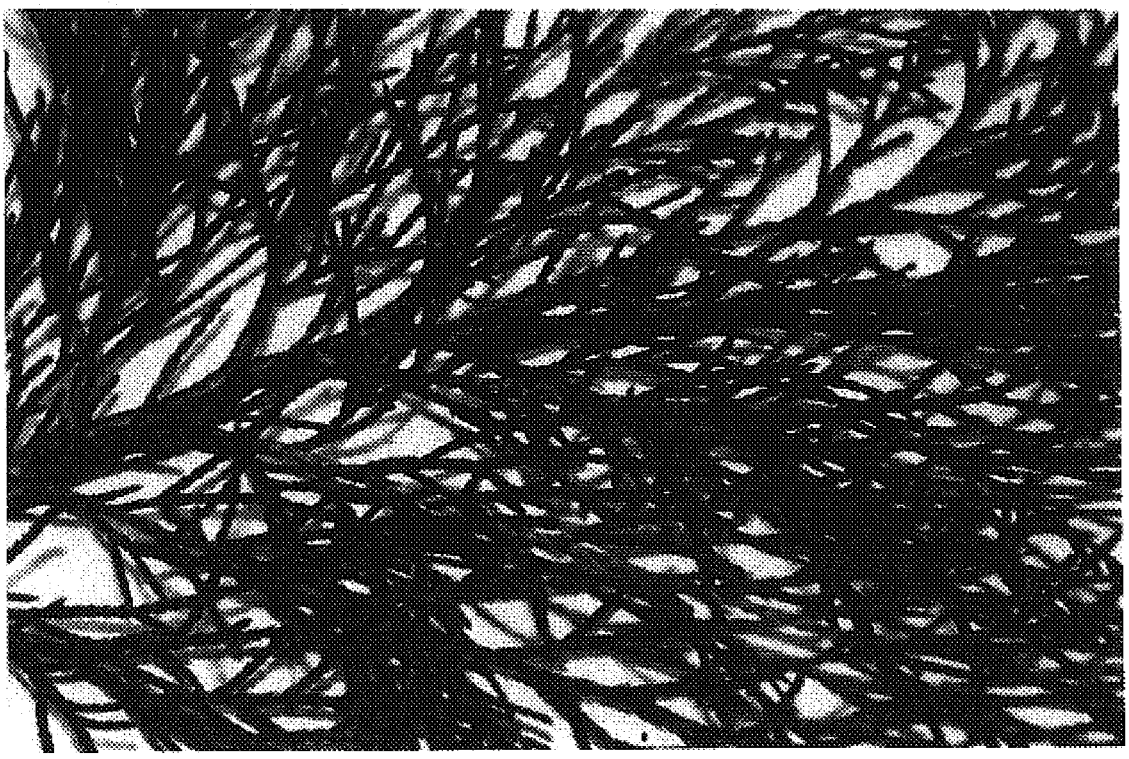
FIG. 4 shows for comparative purposes typical foliage of the *Microbiota decussata* plant during the winter.

The following is a detailed description of the new cultivar of the present invention which was prepared while observing primarily during September 2007 and January 2008 approximately five year-old container-grown plants at West Grove, Pa., U.S.A., which had been reproduced by the rooting of cuttings. Color terminology is in accordance with the R.H.S. Colour Chart of The Royal Horticultural Society, London, England, except where general color terms are used which are to be accorded their customary dictionary significance.

Type: Evergreen conifer shrub with a low crown.

Plant:

*Growth habit.*—Low-growing, creeping, generally prostrate.

*Height.*—Commonly approximately 12 inches.

*Width.*—Commonly approximately 24 inches, and sometimes more.

*Twig presentation.*—Substantially horizontal.

*Mature branch presentation.*—Substantially horizontal.

*Twig color.*—Greyed-Orange Group 177B.

*Young branch color.*—Greyed-Orange Group 176D.

*Mature branch color.*—Commonly near Greyed-Orange Group 177A and Grey-Orange Group 177B.

*Twig diameter.*—Commonly approximately 1 mm on average.

*Main branch diameter.*—Commonly approximately 5 mm on average.

*Secondary branch diameter.*—Commonly approximately 3 mm on average.

*Twig texture.*—Substantially smooth.

*Main branch texture.*—Substantially smooth.

*Secondary branch texture.*—Substantially smooth with some exfoliating bark.

*Degree of branching.*—Medium dense and generally arranged at a plurality of horizontal levels.

*Arrangement.*—Branchlets arranged in flattened sprays.

*Length.*—Commonly approximately 8 mm on average.

*Width.*—Commonly approximately 1 mm on average.

*Base.*—Truncate.

*Apex.*—Acuminate.

*Margin.*—Entire.

*Texture.*—Smooth on upper and under surfaces.

*Summer color.*—Green Group 138A.

*Winter color.*—Greyed-Orange Group 165A with overtones of Blue-Green Group 122A.

*Fragrance.*—Somewhat resembles resin when rubbed or when cut.

Inflorescence:

*Cones.*—None available for observation.

*Seeds.*—None available for observation.

Development:

*Hardiness.*—U.S.D.A. Hardiness Zone Nos. 3 to 8.

*Propagation protocol.*—Asexually reproduces well during the winter by the use of semi-hardwood cuttings with the aid of Hormodin No. 3 rooting hormone and bottom heating at 70° F.

*Disease resistance.*—No particular susceptibility has been noted during observations to date.

*Pest resistance.*—No particular susceptibility has been noted during observations to date.

*Usage.*—Ornamental for growing as a specimen plant or as a ground cover.

Plants of the new 'Condrew' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct Siberian Cypress plant possessing the following characteristics:

(a) displays a creeping prostrate growth habit, (b) forms attractive foliage that is bluer in coloration particularly at the juvenile stage and during the winter months, and (c) is well suited for growing as a specimen plant or in a group as a ground cover;

substantially as illustrated and described.

* * * * *